United States Patent [19]

Bradshaw et al.

[11] 4,271,357
[45] Jun. 2, 1981

[54] TRACE VAPOR DETECTION

[75] Inventors: Robert F. D. Bradshaw, Markyate; Alec Kraicer, Edgeware, both of England

[73] Assignee: Pye (Electronic Products) Limited, Cambridge, England

[21] Appl. No.: 18,801

[22] Filed: Mar. 8, 1979

[30] Foreign Application Priority Data

May 26, 1978 [GB] United Kingdom ............... 23040/78
May 31, 1978 [GB] United Kingdom ............... 24764/78

[51] Int. Cl.³ .......................... B01D 59/44; H01J 49/00
[52] U.S. Cl. ..................................... 250/287; 250/282; 250/283
[58] Field of Search ............... 250/281, 282, 283, 287, 250/294, 423 R, 424, 427

[56] References Cited
U.S. PATENT DOCUMENTS

| 3,522,425 | 8/1970 | Rich | 250/281 |
| 3,668,385 | 6/1972 | Cohen | 250/282 |

Primary Examiner—Bruce C. Anderson
Attorney, Agent, or Firm—Thomas A. Briody; Robert T. Mayer; Paul R. Miller

[57] ABSTRACT

An apparatus is provided for detecting trace quantities of chemical species in the form of a vapor by subjecting ions produced in a sample of the mixed gas under flow to an ion repulsive electric field which is directed in the opposite direction to the flow of the gases, and comprises a fan for drawing the sample through a hollow body, having an inlet, a first region containing means for ionizing at least a proportion of the molecules of the sample by a corona discharge, a second region in which the sample is subjected to an oppositely directed ion repulsive electric field and a third region having an electrode for collecting ions of selected polarity. Ions of a selected polarity whose ionic mobilities exceed a value dependent on the strength of the ion repulsive electric field and the velocity of the gas flow are prevented from entering the third region. A resistor may be provided to limit the current of the corona electric discharge to a value not greater than 100 nanoamps.

23 Claims, 4 Drawing Figures

TRACE VAPOR DETECTION

The present invention relates to an apparatus and to a method for detecting trace quantities of a chemical species in the form of a vapor in an oxygen-containing gaseous mixture by subjecting ions produced in a sample of the mixed gases under flow to an ion repulsive electric field, in which the ion repulsive electric field is directed in the opposite direction to the flow of the gases. For the purpose of the present invention the expression, "chemical species" refers to vapor molecules of substances which are capable of forming relatively stable ions in the presence of oxygen when under the influence of an applied electric field; such ions of the chemical species having a mobility which is low compared with the mobility of other ions which may be produced in the oxygen containing gaseous mixture by the applied electric field.

Included in such species are certain substituted hydrocarbons which have at least one strongly electro-positive or electro-negative atom or atom group in their molecules and also the heavier halogens such as, bromine and iodine.

Apparatus embodying the invention may be used to determine the presence of substances in the form of solids, liquids or mixtures thereof which substances emit the aforesaid chemical species in the form of a vapor at normal temperature and pressure. Such substances include, for example, explosive substances for example, dynamite, toxic vapors, for example, certain narcotic drugs, and pesticides.

The apparatus may also be employed for detecting leaks into the atmosphere of gases which contain the chemical species as, for example, a tracer substance, such as a heavy halogen, from pipelines, chemical plant and the like.

It is known that when a sample of atmospheric gases containing traces of chemical species of the aforesaid kind is ionised, e.g. by an applied electric field in the form of a corona discharge, ions are formed from the molecules of the chemical species together with ions of the other constituents of the atmosphere. In general, the various ions present will have differing ionic mobilities. It is also known to use an ion repulsive electric field technique to measure the mobilities of the various ion species created in a corona discharge, for example as described in a paper by A. Goldman, R. Haug and R. V. Latham published in Journal of Applied Physics, Vol. 47 No. 6, June 1976. In this paper there is described a method for recording the inverse mobility spectra of ion species present in a continuous gas-flow situation. The spectra obtained are from oxygen and nitrogen and from air environments. No further explanation is given in regard to the gas compositions used other than confirming that unspecified impurities may be contained in the gas mixture.

One subject of the present invention is to provide an apparatus which can detect the presence of chemical species of the aforesaid kind in an oxygen-containing gaseous mixture by subjecting ions of the aforesaid chemical species, when in a continuous gas flow situation, to a ion repulsive electric field. The apparatus and method of the present invention utilizes the fact that the mobility of ions formed from such species is relatively low compared with the mobility of ions formed from other constituents of the gaseous mixture.

Another object of the present invention is to provide a method of detecting trace quantities of chemical species of the aforesaid kind in an oxygen-containing gaseous mixture by selecting ions of one polarity of the chemical species so that they can be carried with the gaseous mixture through an ion repulsive electric field.

According to the present invention there is provided an apparatus for detecting trace quantities of chemical species in the form of a vapor contained in an oxygen-containing gaseous mixture by subjecting ions produced in a sample of the mixed gases under flow to an ion repulsive electric field, with the repulsive field being directed in the opposite direction to the flow of the gases, characterized in that there is provided means for drawing the sample through a hollow body, the hollow body having serially arranged an inlet, a first, a second and a third internal region and an outlet, the first region containing means for ionising at least a proportion of the molecules of the sample including molecules of the chemical species and means for selecting ions of one polarity for travel with the sample into the second region, means for promoting flow of the sample through the second region as a jet of substantially uniform velocity, means for producing in the second region the oppositely directed ion repulsive electrid field, and means in the third region for collecting ions of selected polarity, the arrangement being such that, in operation, ions of the one selected polarity whose ionic mobilities exceed a value dependent on the strength of the ion repulsive electric field and the velocity of the gas flow can be prevented from entering the third region.

In one arrangement the apparatus is portable, light in weight and operates without a bottled gas supply. The apparatus can be relatively simple in construction and economical to manufacture and it is particularly advantageous when the apparatus is applied to detecting trace quantities of chemical species emitted from explosive type substances in that only a short warm-up time is required to detect the chemical species.

The hollow body may comprise first and second tubes of an electrically conducting material joined in end to end relationship by a ring of insulating material with the first region being located within the first tube and the second and third regions being located within the second tube.

The first tube may be provided at the end remote from the second tube with an end wall having an inlet aperture for admitting the sample to the first region and at the end adjacent to the second tube with a disc of an electrically conducting material and the disc being positioned transverse to the gas flow and having at least one aperture for admitting the sample to the second region.

Each aperture of the disc at the end adjacent the second tube is shaped so that the sample can pass through the second region in a stream-lined manner and with a substantially uniform velocity.

The second and third regions may be partially separated by a further disc of an electrically conducting material located at a point remote from the ends of the second tube and having at least one aperture leading from the second region to the third region for admitting the sample to the third region the disc being in electrical contact with the wall of the tube.

The means for drawing the sample through the hollow body may be an electrically driven fan which can be positioned substantially at the outlet of the hollow body.

The means for ionising at least a proportion of the molecules of the sample including molecules of the chemical species may be an electrode located in the first region or a radio active source located in the first region. When a ratio active source is used there is also provided in the first region means for selecting ions of one polarity from a bi-polar ion population produced by the radio activity.

The means for selecting ions of one polarity for travel with the sample into the second region may be an electric field produced by a high direct voltage applied to an electrode in the first region.

Where the ionising means is an electrode which in operation produces a corona discharge it can be advantageous to limit the discharge current to not more than 100 nanoamps and; in some cases it has been found advantageous to limit the current to not more than 30 nanoamps. The current-limiting can be effected by inserting a resistor between a high voltage source and the discharge electrode.

When a radio active ionising source is used the disc between the first and second regions is electrically insulated from the wall of the first tube and is maintained at a direct current electric potential relative to the wall so that ions of one polarity are attracted towards the disc and ions of the opposite polarity are repelled from the disc. The further disc can be maintained at an electrical potential relative to the first disc so as to produce an electric field in the second region which produces a force on the ions of the one selected polarity in a direction opposite to that of the flow of the gas sample.

The wall of the second region conveniently is connected to a first pole of a direct current electrical power supply of negative or positive potential polarity for negative or positive charged ions respectively and the wall of the first region is connected to a second pole of the electrical power supply of an appropriately opposite potential to the first pole. The two walls may be maintained at the appropriate potential by one electrical power supply situated outside the hollow body and connected thereto by electrical cables.

An electrode can be provided in the third region conveniently axial with the aperture to collect ions of the one selected polarity. The electrode may have an insulated lead which passes through the wall of the hollow body and can be electrically connected to a source of direct current potential to attract the ions of selected polarity and to means for measuring changes in the electrical current.

Thus, in one embodiment the electrode is connected to an input of a current amplifier, and an output of the amplifier is connected to indicating means so as to measure changes of current flow from the electrode.

The amplifier can be arranged to have a relatively low gain when the current fed to its input is constant and a substantially higher gain corresponding to variations in its input current.

Conveniently feedback means may be connected between an inverting input of the amplifier and a tapping point on a potentiometer chain connected between an output of the amplifier and a common rail, with the potentiometer chain including a capacitor connected in the section between the tapping point and the common rail.

The electrode can be connected to the input of the amplifier and the common rail connected to the source of d.c. potential.

The apparatus may include means for discharging the capacitor when the current collected by the electrode is reduced.

This embodiment may also include means for comparing the potential on the capacitor with the potential at the output of the amplifier and means for discharging the capacitor when its potential exceeds that at the output of the amplifier.

This arrangement may also include means for preventing the capacitor being charged by power supply surges which can occur when the apparatus is switched on.

A switch means which is effective when the apparatus is switched on to connect a low impedance path across the capacitor and to disconnect the path when the power supply to the apparatus has reached a steady state may also be included.

According to a further aspect of the invention there is also provided a method for detecting trace quantities of chemical species in the form of a vapor in an oxygen-containing gaseous mixture by subjecting ions produced in a sample of the mixed gases under flow to an ion repulsive electric field with the repulsive field being directed in the opposite direction to the flow of gases characterised by the steps of drawing the gaseous mixture through the hollow body as hereinbefore defined wherein a proportion of the molecules of the chemical species are ionised in the first region and ions of one polarity are selected for onward travel with the sample of the gaseous mixture, passing the gas flow at a substantially uniform velocity through the second region wherein an electric field is established effective to urge ions of the selected polarity in a direction opposite to that of the gas flow and through to a third region to which the electric field does not extend, and detecting ions whose ionic mobilities are sufficiently low so that they are carried by the gas flow through the electric field in the second region. In the method a mixture of atmospheric gases containing trace quantities of the chemical species may be used.

Compositions which generate a smoke can be detected, for example, by fumigating candles or fumigating powders which emit a smoke of compounds when burning. The compounds emitted may be mixed with the products of a combustible mixture e.g. a fuel such as, sugar or wood in a ground form, together with substances to maintain combustion, such as, ammonium nitrate or potassium chlorate, and/or substances to delay combustion, such as, kaolin, bentonite and/or silicic acid.

Compositions containing trace quantities of the chemical species may be detected from sprayed pesticidal preparations. It is known, in the control of noxious organism, in agriculture, horticulture or forestry that large areas to be treated can be sprayed with aqueus solutions or dispersions of pesticides. The amount of liquid used can vary widely and may result in an application of from 40 liters to 1000 liters per hectare. These solutions may be applied by spraying from ground machines or from aircraft and frequently are applied from Ultra-low-volume concentrates. Such preparations generally break up as a mist of very small drops on application and the drops may have diameters of only about 100 μm while still in the vaporized form. Trace quantities of the aforesaid chemical species may be readily detected by the method and apparatus according to the present invention.

The presence of aerosol compositions may also be determined particularly when the aerosol compositions containing the chemical species are prepared in the conventional manner and contain the active substance, with a solvent and a volatile fluid as the propellant, for example, chloro-fluoro derivatives of methane or ethane.

Embodiments of the invention and the manner in which it is to be performed will now be described with reference to the accompanying drawings, in which:

FIG. 1 is a sectional drawing of a detection apparatus embodying the invention;

FIG. 2 is a circuit diagram embodying the invention,

FIG. 3 is a more detailed schematic diagram of an amplifier unit for use in the apparatus of FIG. 1, and FIG. 4 is a sectional drawing of a further embodiment of the invention.

Referring first to FIG. 1, the detection apparatus comprises a generally cylindrical body 1 formed by coaxial tubes 2 and 3 of electrically-conducting material such as iron, copper or aluminum or alloys thereof joined in end-to-end relationship by a ring 4 of an insulating material. The tube 2 is provided at its free end with an end-wall 5 of conductive material provided with a central aperture 6. An inlet nozzle or probe 7 coaxial with the aperture 6 is provided on the outer face of the end wall 5. The nozzle 7 may be of insulating material or of a conducting material such as a metal, in which case it is insulated from the end wall 5 by an insulating spacer ring 8.

At the end of the tube 2 adjacent the tube 3 there is provided a septum 9 comprising a metal disc having an axial aperture 10, and the septum 9 is electrically connected to the wall of the tube 2.

A baffle 11 is located at a point intermediate the ends of the tube 3 which baffle 11 comprises either a metallic disc having at least one aperture 12 or a sheet of metallic gauze or a grid like structure with the circumference of the baffle conveniently being electrically connected to the wall of the tube 3.

A fan 13 driven by an electric motor 14 is located within the tube 3 adjacent its open end and is effective to draw a sample of the atmosphere into the apparatus through the nozzle 7 and thence successively through a first region 15 within the body 1 defined by the end-wall 5 and the septum 9, through a second region 16 defined by the septum 9 and the baffle 11, through a third region 17 defined by the baffle 11 and the fan 13 and the sample through the open end of the tube 3 to expel the sample.

The aperture 10 of the septum 9 can be profiled so that the sample passes through the region 16 as a single smooth jet of substantially uniform velocity, as indicated by the arrow 18. Suitable contours for the aperture 10 are shown in British Standards Specification No. 1042 at p. 141 the contents whereof are incorporated by reference herein. In an alternative arrangement, the septum 9 has a plurality of apertures each regularly profiled so that the sample passes through the region 16 as a corresponding plurality of smooth jets of uniform velocity. In order to smooth the flow at the upstream side of the septum 9, a grid 19 having a plurality of parallel passageways is provided in the aperture 6.

A pointed electrode 20 is located in the region 15, being supported by a lead 21 which passes through an insulator 22 mounted in the wall of the tube 2. Outside the tube 2, the lead 21 is connected by a resistor 71 to one side of a high voltage supply unit 23 whose other side is connected to a common earth point or ground. The supply unit 23 produces a sufficiently high voltage V3 for example, 3000 V, for a corona discharge to occur from the electrode 20 and to cause ionisation of a proportion of the molecules (including molecules of the aforesaid chemical species) which constitute the sample being drawn through the region 15.

Other suitable high voltages used for producing an ionising corona discharge may be between 2000 V and 5000 V.

The resistor 71 has a value R chosen so that the current $I_D$ of the corona discharge is less than 100 nanoamps and preferably is less than 30 nanoamps.

The current $I_D$ depends on the output voltage $V_3$ of the supply unit 23, the value R of the resistor 71 and also to some extent on the shape of the pointed electrode 20, which affects the striking potential of the discharge. This shape may change in use, due for example to erosion of the electrode, with consequent changes in the value of $I_D$.

A further source of changes in $I_D$ is the supply unit 23, which may conveniently comprise an EHT generator unit energised from a low voltage source such as a 12 V battery, which as will be described more fully hereinafter, may also be used to energise other parts of the apparatus. Such EHT generator units are well-known to those skilled in the art and need not be further described herein. The output voltage $V_3$ of such a unit may vary from its nominal value as the state of charge of the battery varies with use.

For these reasons, for a particular nominal value of $V_3$ and a given value of R, the discharge current $I_D$ may fall within a range of values.

Typical ranges for the value of $I_D$ for various values of R and a nominal value of 3000 V for $V_3$ are as follows:

| | |
|---|---|
| R = 0 | $I_D$ = 2 to 5 microamps |
| R = 50 Gigohms | $I_D$ = 20 to 30 nanoamps |
| R = 100 Gigohms | $I_D$ = 10 to 15 nanoamps |

Preferably, therefore, the value of the resistor 71 is in the range 50 to 100 Gigohms.

As the molecules of the chemical species are present in the sample only in small concentration it would be difficult to achieve appreciable levels of ionisation of species molecules by direct ionisation. To do this the extremely powerful discharge needed to ionise the species molecules would also cause a massive ionisation of the air gases. This is avoided by allowing the discharge to ionise a proportion of the air gases so that a charge exchange reaction can take place in which charge exchange reaction the charges on air ions are transferred to molecules of the species. Considering negative ions, ionisation of molecules of species present in low concentration can take place by this means if the molecules of such species have a greater electron affinity than any of the molecules present in relatively massive numbers, i.e. the air molecules. Electrons present in a gas will rapidly transfer to the molecules with the greater electron affinity.

Moreover, if two chemical species having differing electron affinities are present in the sample in trace quantities, each of, for example, 1 in $10^9$ mole per mole, ion populations of both may be created, provided that both have greater electron affinities than any of the molecules present in massive numbers, because collisions between molecules of the species having the higher electron affinity with ions of the species having the lower electron affinity (in which the ion could be robbed of an electron) will, due to the low concentration of both species, by much less frequent than collisions between molecules of either species and air ions, in which molecules of either species may be ionised.

Similar considerations apply to positive ion populations.

Because of the tendency of ionic charge to migrate to a molecule of greater affinity, a significant proportion of the molecules of a chemical species of the type specified which are present in an air sample drawn through the region 15 becomes ionised.

Consider for example the case of a species present in air at a numerical concentration (molecules per molecule) of 1 in $10^9$. The corona discharge from the electrode 20 may typically create a primary (i.e. air) ion density of 1 ion per $10^8$ molecules of air in the region 15. Assume that one tenth of the species molecules present becomes ionised by charge exchange reactions. The numerical concentration of species ions is thus 1 in $10^{10}$ molecules. The concentration of the primary ions remains substantially unchanged at 1 in $10^8$ molecules. Hence the species ions comprise 1 in $10^2$ of all ions present. The detection problem has thus been changed from detecting one molecule in $10^9$ to that of detecting one in $10^2$ which is an improvement of $10^7$ times.

Although the primary (air) ion population generated by the corona discharge in the region 15 will initially be bipolar, the very high negative potential of the electrode 20 relative to the tube 2, and the resulting intense field in its vicinity causes positive ions to migrate to the electrode 20 where they are neutralised. Thus substantially only negative primary ions travel with the air flow towards the aperture 10 of the septum 9. During the travel of the negative primary ions towards the septum, a proportion of the species molecules present in the air flow will become ionised by the charge-exchange reactions as described hereinbefore. Thus there will arrive at the aperture 10 a mixture of negative primary (air) ions and negative secondary ions created from the molecules of the chemical species.

In the absence of an electric field, these ions would be carried by the jet flow 18 across the region 16 and through the baffle 11 into the third region 17. In this region 17 there is provided an electrode 24 which may comprise a wire, a grid or a plate and which is connected by a lead 25 which passes through an insulator 26 in the wall of the tube 3 to an input terminal 27 of a current amplifier unit 28. The amplifier unit 28 may have a common terminal connected to a relatively low positive potential with respect to the tube 3, for example 5 volts, as indicated schematically in FIG. 1 by the battery 29, so that the input terminal 27 and with it the electrode 24, is also held positive with respect to the tube 3. The electrode 24 is thus effective for attracting negative ions entering the region 17. Such ions collected by the electrode 24 will produce a change in the input current to the amplifier unit 28. The resulting change in the output current of the amplifier unit may be observed by means of a meter 30 and/or may be utilised to trigger an alarm circuit 31 effective to produce a signal, such as an audible or a visible signal.

Figure 1:
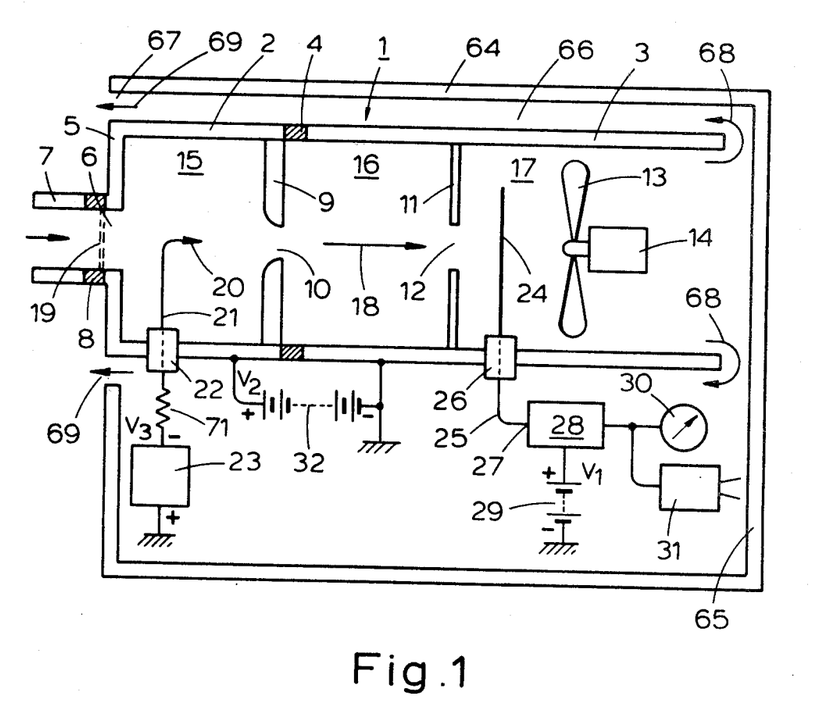

A source of potential, typically, 300 volts, indicated schematically by a battery 32 is connected between the tube 2 and the tube 3 so that the tube 3, and with it the septum 9 is positive with respect to the tube 2 and in particular to the baffle 11. An electric field is therefore produced in the region 16. Although there are fringing effects near the wall of the body 1, the field in the vicinity of the jet 18 is substantially parallel to the axis of the jet and is effective to urge negative ions in a direction opposite to that of the jet flow.

The strength of the electric field in the vicinity of the jet 18 is determined by the separation between the septum 9 and the baffle 11 and the potential $V_2$ of the source 32. This may be for example, 300 volts per cm. For a given field strength ions whose ionic mobilities have a certain critical value will be driven by the field at exactly the velocity of the jet flow, but in the opposite direction. A suitable jet flow velocity is between 300 to 400 cm per second. Such ions will remain stationary so far as motion parallel to the jet axis is concerned. Their random transverse motion may move them laterally into a region of slower gas flow, and the field in this region may then drive them back to the septum 9. Consequently, higher mobility ions are substantially prevented by the field from reaching the baffle 11 and entering the region 17.

Ions which have mobilities higher than the critical value are prevented from entering the region 17, since they are driven back by the field in the region 16 at a velocity greater than that of the jet flow.

Ions with mobilities lower than the critical value are given a velocity by the field in the region 16 lower than the velocity of the jet flow. Although some such ions may be carried by random transverse motions into regions where the velocity of the gas flow is less than the velocity imparted to them by the field, in general those ions whose mobilities are lower than the critical value will be carried by the jet flow across the region 16, albeit at a velocity less than that of the jet flow, and will enter the region 17 and be collected by the electrode 24.

It will be seen that for a given field strength and a given geometry in the region 16, ions with mobilities equal to or exceeding a critical value have no possibility of reaching the electrode 24. For ions of mobilities lower than the critical value there is a finite possibility which increases as the mobility of the ion, and hence the time taken for it to transverse the region 16, decreases.

In use of the value of the potential $V_2$ of the source 32 is chosen to produce a field strength such as to exclude nearly all the primary (air) ions from the region 17 but to allow heavier, less mobile ions, such as those produced from chemical species of the type specified to enter the region and reach the collector electron 24. Such ions manifest themselves as an increase in the output current of the amplifier 28 which may be observed on the meter 30 and which may be employed to trigger the alarm circuit 31.

A sample of air drawn through the apparatus the meter 30 produces a substantially constant low current (background current) which is indicated by meter 30. If desired the meter may be offset either mechanically or electrically to give a zero reading under these conditions.

When a sample of air including trace quantities of chemical species of the type specified is drawn through the apparatus, the meter reading will increase by an amount dependent on the concentration of the species.

The alarm circuit 31 may be arranged to produce the alarm signal when the output current of the amplifier unit 28 exceeds a threshold level which is greater than the background current level.

The apparatus so far described with reference to FIG. 1 is adapted to detect the presence of chemical species which will form negative ions by charge exchange reactions. Any positive ions which may be formed in the region 15 ae attracted to the discharge electrode 20 and do not proceed into the region 16. To adapt the apparatus to detect species which will form positive ions it is necessary merely to reserve the polarities of the high voltage supply unit 23 and of the voltage sources 29 and 32.

The amplifier unit 28 is preferably of a type having a high degree of d.c. stability (low drift) and a relatively high gain, so that small changes in its input current such as may be caused by the presence of very low concentration of chemical species of the type specified may produce significant changes in the amplifier output current which are not masked by variations of the background current caused by drift in the amplifier unit.

Figure 2:
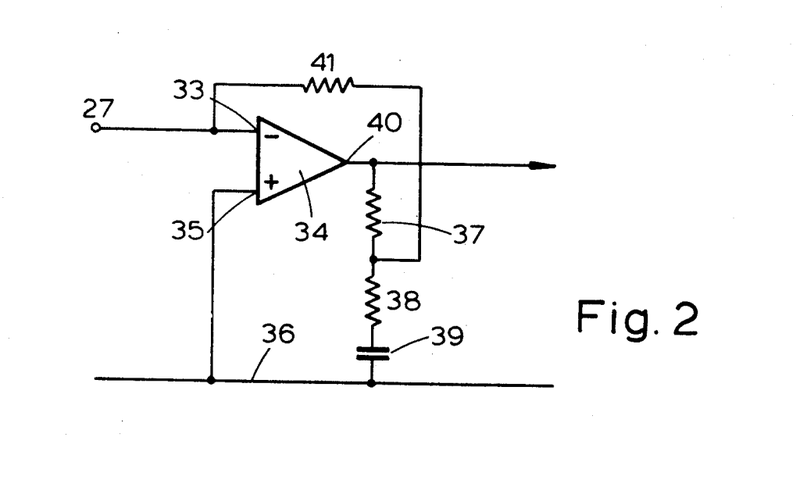
Figure 3:
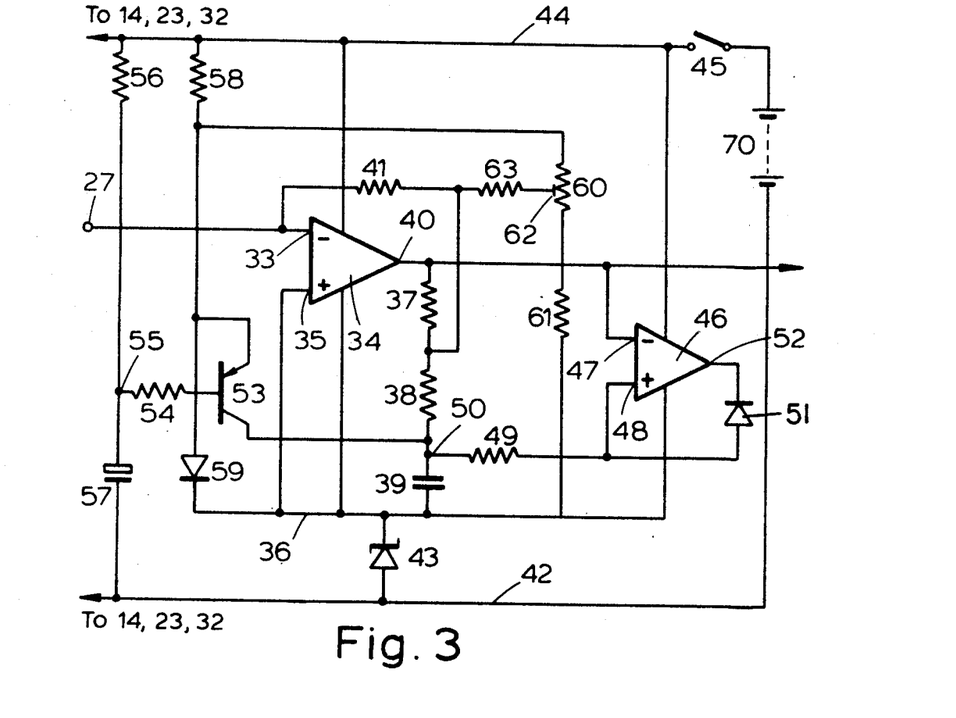

FIG. 2 illustrates a basic arrangement and FIG. 3 is a more detailed schematic diagram of a current amplifier for use as the amplifier unit 28. Referring first to FIG. 2, the terminal 27 is connected to an inverting input 33 of an operational amplifier 34, whose non-inverting input 35 is connected to a common rail 36. Resistors 37 and 38 and a capacitor 39 are connected in series between an output terminal 40 of the operational amplifier 34 and the common rail 36. A feedback resistor 41 is connected between the junction of the resistors 37 and 38 and the inverting input 33. Typically a Burr-Brown amplifier Type 3527 AM may be employed as the amplifier 34. The resistors 37, 38 and 41 may have respective values of 33 M ohm, 330 K. ohm and 500 M. ohm and the capacitor 39 may have a value of 47 μF.

Since at zero frequency the capacitor 39 is effectively an open circuit, it will be seen that the arrangement has a d.c. gain of unity, and consequently has high d.c. stability (low drift). At frequencies for which the impedance of the capacitor 39 is small compared with that of the resistor 38, the gain will be determined by the ratio of the resistors 37 and 38. For the values given by way of example hereinbefore it will be seen that the gain of the arrangement will be 100 for frequencies down to a small fraction of 1 Hz.

Certain difficulties arise if the arrangement of FIG. 2 is employed in the amplifier unit 28. If an atmospheric sample containing chemical species of the type specified is drawn through the apparatus, the resulting negative ions reaching the electrode 24 will cause a negative going current pulse to be applied to the input terminal 27. At the leading edge of the pulse, the output terminal 40 will go positive, charging the capacitor 39. At the end of the pulse, the output terminal 40 will not immediately return to its rest value (background current) but will be held positive by the charge on the capacitor 39. Consequently in this embodiment the apparatus will be unable to respond to a second sample until such time as the charge on the capacitor 39 produced by a first sample has leaked away.

Using the component values cited, and neglecting any internal leakage in the capacitor 39, it will be seen that the apparatus may require several hours to recover.

A similar effect may occur when the apparatus is first switched on, because the initial surge of current may leave the capacitor 39 with a positive charge, and it will be necessary to wait until this charge has leaked away before the apparatus becomes operational. The arrangement of FIG. 3 provides a means of overcoming both these defects.

Turning to FIG. 3, in which integers already described are accorded the same reference numerals as in FIG. 2, it will be seen that the operational amplifier 34, the resistors 37, 38 and 41 and the capacitor 39 are connected as described with reference to FIG. 2. The common rail 36 is connected to the negative bus 42 of a d.c. supply by a zener diode 43. The positive supply terminal of the amplifier 34 is connected to the positive bus 44 of the supply by a switch 45. The common rail 36, and with it the input 33 of the amplifier 34 is therefore held positive to the negative bus 42 by the zener voltage $V_1$ of the diode 43 (typically 5 V). The bus 42 is connected to ground and to the tube 3 (FIG. 1). Thus the electrode 24 is held at a positive potential $V_1$ with respect to the tube 1 and the zener diode 43 comprises the voltage source 29 of FIG. 1.

A further amplifier 46 has its inverting input 47 connected to the output terminal 40 of the amplifier 34. A non-inverting input 48 of the amplifier 46 is connected by a resistor 49 to the junction 50 of the resistor 38 and the capacitor 39. A diode 51 is connected between the output terminal 52 of the amplifier 46 and its non-inverting input 48, the arrangement being such that when the input 47 is positive relative to the input 48 the diode 51 is non-conducting. When the input 48 is positive relative to the input 47, i.e. the capacitor 39 is charged positive relative to the output 40 of the amplifier 34, the diode 51 is conductive and the capacitor 39 is discharged by the resistor 49, which typically has a value of 33 K. ohm. Although the capacitor 39 becomes charged when a negative-going current pulse is applied to the input terminal 27, it now rapidly becomes discharged after the end of the pulse, so that the apparatus can respond to a further sample.

To prevent the capacitor 39 becoming charged when the swtich 45 is first closed, a p-n-p transistor 53 is provided, with its collector connected to the junction 50. The base of the transistor 53 is connected by a resistor 54 to the junction 55 of a resistor 56 and a capacitor 57 which are connected in series between the positive bus 44 and the negative bus 42. A resistor 58 is connected between the positive bus 44 and the emitter of the transistor 53. A diode 59 has its anode connected to the emitter of the transistor 53 and its cathode to the common rail 36.

When the switch 45 is closed, the junction 55 and with it the base of the transistor 53 will initially be at the potential of the negative bus 42. The transistor 53 will therefore conduct and will clamp the junction 50 at the potential of the common rail 36. The potential of the junction 55 will rise as the capacitor 57 charges by the resistor 56, eventually cutting off the transistor 53 and so removing the clamp from the junction 50. The values of the resistor 56 and the capacitor 57 are chosen so that the transistor 53 remains conductive at least until the amplifier 34 has reached its steady-state condition following the closure of the switch 45, thus preventing the accumulation of any charge on the capacitor 39 due to switching-on urges.

To facilitate setting up of the steady-state condition of the amplifier unit (background current) a potentiometer 60 may be provided. One end of the potentiometer may be connected to the positive bus through the resistor 58 and the other end to the common rail 36 through a resistor 61, the resistors 58 and 61 serving to restrict the voltage excursion which may be obtained by adjustment of the position of the slider 62. The slider is connected through a resistor 63, typically of 33 M.ohm to the junction of the feedback resistor 41 and the resistors 37 and 38. By adjustment of the potentiometer 60 the background current level may be set to a desired value.

The negative (42) and the positive (44) buses may be connected to corresponding terminals of a battery 70 of for example 12 V output. The battery 70 may also be employed to energise, by the on-off switch 45, the motor 14 and the voltage sources 23 and 32 (FIg. 1). The voltage source 23, which provides the high voltage necessary to produce the corona discharge in the region 15, may conveniently comprise an EHT generator circuit such as is well known to those skilled in the art, and need not be described further herein. Similarly the voltage source 32 may comprise an EHT generator or d.c. to d.c. converter of known type.

Investigations have shown that the influence of external air currents is greatly reduced if the sample is exhausted to atmosphere is a region adjacent to, and subject to substantially the same external conditions as, the inlet nozzle and to this end the body 1 is surrounded by an outer casing 64. The casing 64 has an end wall 65 spaced from the open outlet end of the tube 3 so as to provide a passageway for the flow of air exhausted by the fan 13 into the annular space 66 between the body 1 and the outer casing 64 and thence to atmosphere via an annular aperture 67 surrounding the inlet end of the body 1. The flow path of the exhaust air is indicated by the arrows 68, 69.

Conveniently, the battery 70, the voltage sources 23 and 32, the amplifier unit 28 and the alarm unit 31 may be located within the outer casing 64 to produce a portable, hand-held apparatus.

Figure 4:
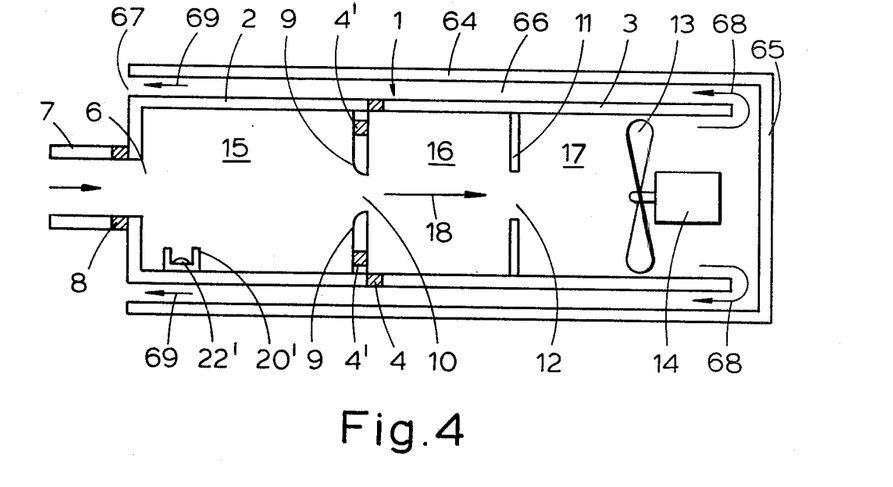

In an alternative arrangement, primary ionisation may be caused by a source of ionising radiation (22' FIG. 4) e.g. a α-particle emitter such as Americium 241, or β-particle emitters such as Nickel 63 or Tritium, located in a container 20' (FIG. 4) within the region 15. Since the primary ion population so produced would be bi-polar, it is also necessary to provide in the region 15 an electric field effective select ions of one polarity for onward travel with the air flow and to prevent ions of the opposite polarity from approaching the septum 9. One method of achieving this is to insulate the septum 9 (FIG. 4) by a ring 4' of insulating material from the tube 2 and to apply a suitable potential therebetween. The septum 9 (FIG. 1) is also insulated from tube 2 when the primary ionisation is caused by a source of ionising radiation located in a container (not shown) in the region 15. The electrode 20, lead 21, insulator 22 and supply unit 23 may then be omitted. The container 20' containing a source of ionising radiation may be inserted into the region 15 through the aperture in the wall 2 (FIG. 1) indicated for the insulator 22. A similar arrangement can be used in the apparatus represented by FIG. 4 and in this case the aperture (not shown) will pass through both wall 2 and wall 64.

This arrangement mitigates problems of preventing leakage of atomic radiation from the apparatus.

Applications of the present invention include anti-terrorist measures such as the screening for explosive substances of travellers and luggage at airway terminals and similar locations, and searching for explosive substances generally. Apparatus embodying the invention may also be employed as a detector in gas chromatography. A further application is in the tracing of leaks in equipment such as pipework, pressure vessels, chemical plants and the like, wherein a tracer substance such as a heavy halogen is introduced into the equipment under test and the apparatus is moved under the exterior of the equipment to detect any escape of the tracer substance.

In a typical experiment with an embodiment of the apparatus as described with reference to FIG. 1, the diameter of the jet orifice 10 was approximately 6 mm and the rate of gas flow through the apparatus was approximately 10 liters/minute. The potential $V_3$ of the corona discharge electrode 20 was 3000 V, the potential $V_1$ of the collector electrode 24 was 5 V and the strength of the repulsive electric field in the region 16 was 300 V/cm. The resistor 71 was shorted out, so that $I_D$ was in the range 2–5 microamps.

When normal atmospheric air was drawn through the apparatus the current collected by the electrode 24 (i.e. the background current) was 1 picoamp.

A sample of a mixture of nitroglycerine vapor in air, having a known concentration of 1 part by weight of nitroglycerine vapor in $10^9$ parts by weight of the mixture was then drawn through the apparatus, and the current of the collector electrode 24 then became 5 picoamps, the rise of 4 picoamps being caused by the presence of the nitroglycerine vapour in the sample.

The experiment was then repeated with the resistor 71 having a value of 50 Gigohms in the circuit so that the discharge current did not exceed 30 nanoamps.

The background current was then 0.3 picoamp, and the current when the nitroglycerine sample was drawn through the apparatus was 1.0 picoamp.

The reduction in background current is due to the lesser noise produced by the limited current corona discharge.

In a further series of experiments, samples of various obtruding substances and also samples of various explosives were presented, firstly to an apparatus in which the resistor 71 was shorted out and secondly to an apparatus in which the resistor was in circuit and had a value of 50 Gigohms. All other parameters of the apparatus were maintained constant throughout the experiments. The results obtained are shown in the following table, in which readings of the meter 30 are listed against the substances. The meter had an arbitrary linear scale from 0 to 100 (=full scale deflection).

| Substance | R = 0 | R = 50 Gigohms |
|---|---|---|
| Solvents | | |
| PCE | 0 | 0 |
| Methanol | 0 | 0 |
| Ethanol | 25 | 8 |
| Xylene | 90 | 0 |
| Nitrobenzene | 25 | 0 |
| White Spirit | 75 | 0 |
| Polishes | | |
| Mansion | 35 | 0 |
| Cherry Blossom Shoe | 75 | 0 |
| Kiwi Shoe | 75 | 0 |
| Brasso | 90 | 0 |
| Turtle Wax Car Polish | 90 | 0 |
| Treble Wax Car Polish | 50 | 0 |
| Duraglit | 99 | 0 |
| Toiletries | | |
| Avon Blue Blazer After-Shave | 15 | 2 |
| Nail Varnish | 75 | 0 |
| Tabac Eau de Cologne | 10 | 0 |
| Chanel No. 5 Eau de Cologne | 35 | 0 |
| Just Musk Perfume | 0 | 1 |
| Indian Summer Perfume | 0 | 4 |
| Azuree Perfume | 35 | 0 |
| Miss Balmain Perfume | 25 | 0 |
| Scandale Spray | 5 | 0 |
| Old Spice After-Shave | 5 | 2 |

-continued

| Substance | R = 0 | R = 50 Gigohms |
|---|---|---|
| Brylcreem | 50 | 3 |
| Nivea Cream | 10 | 0 |
| Old Spice Talc for Men | 25 | 0 |
| Brut After-Shave | 50 | 0 |
| Sunsilk Conditioner | 35 | 2 |
| Pears Hand Cream | 25 | 0 |
| Ultra-Brite Toothpaste | 90 | 3 |
| Disinfectants | | |
| Savlon | 70 | 0 |
| Pine | 35 | 5 |
| Miscellaneous | | |
| Petrol | 15 | 0 |
| Tin of paint (Polyurethane) | 90 | 16 |
| Horseradish Sauce | 15 | 0 |
| Ground Almonds | 5 | 0 |
| Curry Powder | 0 | 0 |
| Chanel No. 5 on Skin Wet | 25 | 0 |
| Chanel No. 5 on Skin Wet after 5 mins | 50 | 2 |
| Chanel No. 5 on Skin Wet after 15 mins | 35 | 5 |
| Chanel No. 5 on Skin Wet after 25 mins | 50 | 4 |
| Explosives | | |
| Needle from Gelignite flask | 75 | 99 |
| TNT | 10 | 6 |
| RDX/TNT | 15 | 8 |
| Double-Based Powder | 90 | 80 |
| Plastic Igniter Cord (Slow) | 25 | 0 |
| Siesmex H.E. | 15 | 0 |
| Polar Ajax | 75 | 85 |
| Minespex | 50 | 36 |
| Wincoal (A) | 50 | 90 |
| Water Gel | 0 | 0 |

Temperatures: 25° C.

All samples were offered as opened containers (except where stated).

Applications of the present invention include the screening for explosive substances of travellers and luggage at airway terminals and similar locations, and searching for explosive substances generally. Apparatus embodying the invention may also be employed as a detector in gas chromatography. A further application is in the tracing of leaks in equipment such as pipework, pressure vessels, chemical plant and the like, wherein a tracer substance such as a heavy halogen is introduced into the equipment under test and the apparatus is moved over the exterior of the equipment to detect any escape of the substance.

We claim:

1. An apparatus for detecting trace quantities of chemical species in an oxygen-containing gaseous mixture comprising:
   a hollow body having serially an input region, a first internal region, a second internal region, a third internal region, and an outlet region;
   means for flowing an oxygen-containing gaseous mixture including trace quantities of chemical species through said hollow body;
   means in said first internal region for ionizing at least a portion of molecules of said gaseous mixtures including said chemical species;
   means for selecting ions of one polarity for travel into said second internal region;
   means between said first internal region and said second internal region for inducing flow of a substantially uniform velocity jet of at least a sample portion of said ionized gaseous mixture and said ionized chemical species through said second internal region into said third internal region;
   means for directing an ion repulsive electric field with respect to non-selected species in an opposite direction to said flow of said sample portion in said second internal region; and
   means in said third internal region for collecting ions of said one polarity which have ionic mobilites of a value permitting travel into said third internal region.

2. An apparatus according to claim 1, wherein said hollow body includes first and second tubes of respective electrically conducting material joined in end to end relationship by a ring of insulating material, said first internal region being contained within said first tube and said second and third internal regions being contained with said second tube.

3. An apparatus according to claim 2, wherein said means in said third region for collecting ions of said one polarity include an electrode electrically connected to a direct potential source, and means for measuring changes in electrical current.

4. An apparatus according to claim 3, wherein said electrode is electrically connected to a circuit including a current amplifier, and said means for measuring changes in electrical current is connected to an output of said amplifier.

5. An apparatus according to claim 4, wherein said amplifier has a relatively low gain for constant input current and a substantially higher gain for variations in said input current.

6. An apparatus according to claim 4, wherein said circuit includes feedback means connected between an inverting input of said amplifier and a tapping point of a potentiometer circuit, said potentiometer circuit being connected between an output of said amplifier and a common rail, and a capacitor connected between said tapping point and said common rail.

7. An apparatus according to claim 6, wherein said electrode is connected to an input of said amplifier, and said common rail is connected to a source of D.C. potential.

8. An apparatus according to claim 6, wherein said circuit further includes means for discharging said capacitor when current collected by said electrode is reduced.

9. An apparatus according to claim 8, wherein said circuit also includes means for comparing potential on said capacitor with potential at said output of said amplifier, and means for discharging said capacitor when said potential on said capacitor exceeds said potential at said output of said amplifier.

10. An apparatus according to claim 6, wherein said circuit includes means for preventing a charging of said capacitor by power supply surges at current switch-on.

11. An apparatus according to claim 10, wherein said means for preventing includes a transistor switching circuit means for connecting a low impedance path to said capacitor when said power supply is switched-on and for disconnecting said low impedance path when said power supply has reached a steady state.

12. An apparatus according to claim 2, wherein said first tube is provided at an end remote from said second tube with an end wall having an inlet opening for admitting said gaseous mixture into said first tube, and at an end adjacent to said second tube said means for inducing flow includes a first disc of electrically conducting material transverse to said flow, said first disc having at least one aperture for admitting said sample portion to said second internal region.

13. An apparatus according to claim 12, wherein said at least one aperture of said first disc is shaped to promote a streamlined flow of said sample portion.

14. An apparatus according to claim 12, wherein said second and third internal regions are at least partially separated by a further electrically conducting disc being located at a point remote from ends of said second tube, said further disc having at least one aperture and being in electrical contact with said second tube.

15. An apparatus according to claim 14 wherein said further disc is maintained at an electrical potential relative to said first disc for producing said ion repulsive electric field in said second internal region.

16. An apparatus according to claim 14, wherein said ion repulsive electric field is formed by a connection of a wall of said second internal region to one pole of a direct current electrical power supply and a connection of a wall of said first internal region to another pole of said direct current power supply.

17. An apparatus according to claim 2, wherein said means for ionizing is an electrode in said first internal region for producing a corona discharge by electrical connection to a high direct voltage supply.

18. An apparatus according to claim 17, wherein means are provided for limiting the corona discharge current to no more than 100 nanoamps.

19. An apparatus according to claim 17, wherein said means for selecting ions of one polarity incudes an electrical field produced by said high direct voltage supply.

20. An apparatus according to claim 2, wherein said means for ionizing includes a radioactive source located in said first internal region, and said means for selecting ions of one polarity select ions from a bi-polar ion population produced by said radioactive source.

21. An apparatus according to claim 20, wherein said means for selecting include a disc between said internal region and said second internal region, said disc being electrically insulated from said first tube, and being maintained at a direct potential relative to said first tube, so that said ions of one polarity are attracted toward said disc and ions of another polarity are repelled from said disc.

22. An apparatus according to claim 1, wherein said means for flowing include an electrically driven fan which is positioned substantially at said outlet region, said fan drawing said gaseous mixture through said hollow body.

23. A method for detecting trace quantities of chemical species in an oxygen-containing gaseous mixture comprising the steps of drawing an oxygen-containing gaseous mixture including trace quantities of chemical species through a hollow body having first, second and third internal regions; ionizing a portion of molecules of said chemical species in said first internal region; selecting ions of one polarity of said chemical species to pass with a sample portion of said gaseous mixture at least at a uniform velocity jet through said second internal region; establishing an electric field with respect to non-selected species in said second internal region in a direction opposite to flow of said gaseous mixture; and detecting in said third internal region ions having sufficiently low mobilities to be carried with said gaseous mixture through said second internal region.

* * * * *

UNITED STATES PATENT OFFICE
CERTIFICATE OF CORRECTION

Patent No. 4,271,357      Dated  June 2, 1981

Inventor(s)  Robert F.D. Bradshaw et al

It is certified that error appears in the above-identified patent and that said Letters Patent are hereby corrected as shown below:

On the Title page, under item [30] Foreign Application Priority Data, change "May 26, 1978" to read --March 15, 1978--

Col. 15, Line 29, before "field" change "trical" to read --tric--

Col. 16, line 4, after "said" insert --first--

Signed and Sealed this

Twenty-fifth Day of August 1981

[SEAL]

Attest:

Attesting Officer

GERALD J. MOSSINGHOFF

Commissioner of Patents and Trademarks